United States Patent [19]

Blank et al.

[11] 4,215,071
[45] Jul. 29, 1980

[54] PROCESS FOR THE PREPARATION OF SULPHONIC ACID CHLORIDES

[75] Inventors: Heinz U. Blank, Odenthal; Theodor Pfister, Wuppertal, both of Fed. Rep. of Germany

[73] Assignee: Bayer Aktiengesellschaft, Leverkusen, Fed. Rep. of Germany

[21] Appl. No.: 941,099

[22] Filed: Sep. 8, 1978

[30] Foreign Application Priority Data

Sep. 28, 1977 [DE] Fed. Rep. of Germany ....... 2743542

[51] Int. Cl.$^2$ .......................................... C07C 143/26
[52] U.S. Cl. .................................................. 260/543 R
[58] Field of Search .................................... 260/543 R

[56] References Cited

U.S. PATENT DOCUMENTS

| | | | |
|---|---|---|---|
| 3,706,794 | 12/1972 | Horner | 260/543 R |
| 3,795,705 | 3/1974 | Chan | 260/543 R |
| 4,105,692 | 8/1978 | Blank | 260/543 R |

OTHER PUBLICATIONS

Groggins, "Unit Processes in Organic Synthesis", p. 224, (4th ed., 1952).

*Primary Examiner*—Paul J. Killos
*Attorney, Agent, or Firm*—Sprung, Felfe, Horn, Lynch & Kramer

[57] ABSTRACT

An improvement in a process for the preparation of the sulphonic acid chloride of the formula

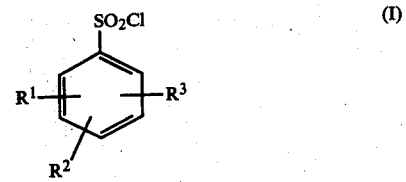

wherein $R^1$, $R^2$ and $R^3$ are identical or different and denote hydrogen, a lower alkyl or cycloalkyl radical, halogen, nitro, aryl, aralkyl, aryl ether or a radical

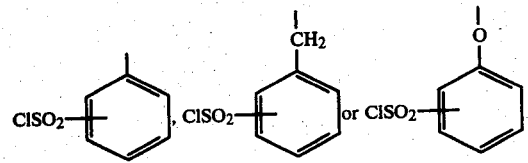

or wherein adjacent radicals $R^1$ and $R^2$ are linked to form a cycloaliphatic or aromatic carbocylic ring which is optionally substituted by a sulphonic acid chloride group by contacting a sulphonic acid of the formula

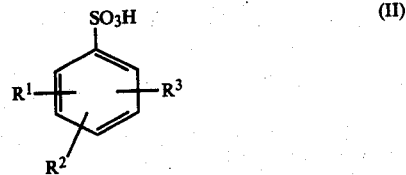

wherein $R^1$, $R^2$ and $R^3$ have the abovementioned meanings, with phosgene in the presence of a N,N-dialkylcarboxylic acid amide catalyst, the improvement wherein the process is carried out in the presence of a sulphonating agent.

5 Claims, No Drawings

PROCESS FOR THE PREPARATION OF SULPHONIC ACID CHLORIDES

The invention relates to a process for the preparation of sulphonic acid chlorides.

It is shown (Houben-Weyl, Methoden der organischen Chemie (Methods of organic Chemistry), volume 9, page 567 (1955)) that when phosgene acts on aromatic sulphonic acids, or their alkali metal salts, in an inert solvent at 140°–180° C., the corresponding sulphonyl chlorides are formed.

It is also known that aromatic sulphonic acid chlorides can be prepared from the corresponding sulphonic acids and phosgene in the presence of dimethylformamide and tertiary amines at temperatures below 100° C. (DT-OS (German Published Specification) 1,963,383).

The preparation of aromatic sulphonic acid chlorides from sulphonic acids and phosgene in the presence of tertiary organic acid amides as catalysts is described in DT-AS (German Published Specification) 1,593,906. In these processes, phosgene is always employed in excess, relative to the sulphonic acids.

A process has been found for the preparation of sulphonic acid chlorides of the formula

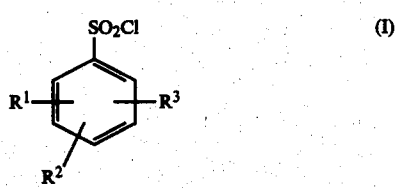

wherein
$R^1$, $R^2$ and $R^3$ are identical or different and denote hydrogen, a lower alkyl radical or a cycloalkyl radical, halogen, nitro-, aryl, aralkyl, aryl ether or a radical

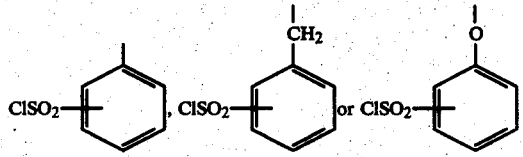

or wherein
adjacent radicals $R^1$ and $R^2$ are linked to form a cycloaliphatic or aromatic carbocyclic ring which is optionally substituted by a sulphonic acid chloride group,
from sulphonic acids of the formula

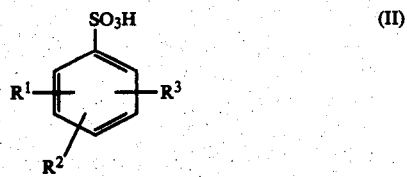

wherein
$R^1$, $R^2$ and $R^3$ have the abovementioned meaning, and phosgene in the presence of catalysts of the N,N-dialkylcarboxylic acid amide class, in which the reaction is carried out in the presence of a sulphonating agent.

Lower alkyl radicals ($R^1$ to $R^3$) can be straight-chain or branched alkyl radical with 1 to 6, preferably 1 to 4, carbon atoms. Examples which may be mentioned are: methyl, ethyl, propyl, iso-propyl, butyl, iso-butyl, pentyl, isopentyl, hexyl and iso-hexyl.

Examples of cycloalkyl radicals ($R^1$ to $R^3$) which may be mentioned are cyclopentyl and cyclohexyl, preferably cyclohexyl.

Halogens ($R^1$ to $R^3$) which may be mentioned are fluorine, chlorine, bromine and iodine, preferably fluorine, chlorine and bromine.

Examples of aryl radicals ($R^1$ to $R^3$) which may be mentioned are phenyl and naphthyl, preferably phenyl.

Examples of possible aralkyl radicals ($R^1$ to $R^3$) are those with 6 to 18 carbon atoms, the aliphatic part of which contains 1 to 6 carbon atoms and the aromatic part of which is a radical from the benzene series. Examples which may be mentioned are the following araliphatic radicals: benzyl, β-ethyl-phenyl, γ-propyl-phenyl and β-phenyl-n-hexyl, preferably benzyl.

An aryl ether radical ($R^1$ to $R^3$) which may be mentioned is, in particular, the phenoxy radical.

Fused ring systems, such as indane, tetralin, indene and naphthalene, preferably naphthalene, are formed by the linking of the adjacent radicals $R^1$ and $R^2$ to give a cycloaliphatic or aromatic ring. The radicals $R^1$ to $R^3$ can be substituted by further radicals which are not changed under the conditions of the process according to the invention. Examples which may be mentioned is halogen, nitro, lower alkyl, aryl, aroxy, alkoxy and aralkyl.

Preferred sulphonic acids which may be mentioned are compounds of the formula

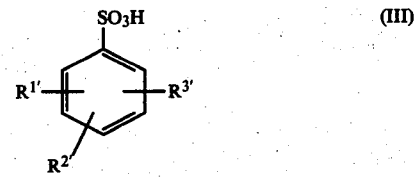

wherein
$R^{1\prime}$, $R^{2\prime}$ and $R^{3\prime}$ are identical or different and denote hydrogen, an alkyl radical with 1 to 4 carbon atoms, fluorine, chlorine, bromine, nitro, phenyl, phenoxy or benzyl,
or wherein
adjacent radicals $R^{1\prime}$ and $R^{2\prime}$ are linked to form a cycloaliphatic or aromatic carbocyclic ring with 6 ring members.

The following sulphonic acids may be mentioned as examples: benzenesulphonic acid, 2-, 3- and 4-toluenesulphonic acid, 2-, 3- and 4-chloro-benzenesulphonic acid, 2,5- and 3,4-dichloro-benzenesulphonic acid, 3-nitro-benzenesulphonic acid, 4-chloro-3-nitro-benzenesulphonic acid, 6-chloro-3-nitrobenzenesulphonic acid, 2-chloro-toluene-4-sulphonic acid, 4-chloro-toluene-2-sulphonic acid, 2-nitro-toluene-4-sulphonic acid, 4-nitro-toluene-2-sulphonic acid, 1- and 2-naphthalenesulphonic acid, 5-nitro-naphthalene-1-sulphonic acid, 5-nitronaphthalene-2-sulphonic acid, 4-biphenylsulphonic acid, 4,4-biphenyldisulphonic acid, 4-phenoxy-benzenesulphonic acid and diphenylmethane-4-sulphonic acid.

Benzenesulphonic acid is a particularly preferred starting material.

Sulphonating agents which may be mentioned are sulphuric acid, sulphur trioxide, chlorosulphonic acid and sulphuryl chloride, preferably sulphuric acid, chlorosulphonic acid and sulphuryl chloride. Mixtures of these sulphonating agents, for example oleum, can also be employed.

In general, one can employ up to approximately 30% by weight, preferably 2–20% by weight and in particular 4–15% by weight, of sulphonating agent in the process according to the invention, the amount of sulphonating agent being relative to the amount of benzenesulphonic acid employed.

The sulphonating agent can be admixed to the sulphonic acid before reaction thereof with phosgene. However, one can add the sulphonating agent during the reaction of the sulphonic acid with phosgene. It is equally expedient to initially introduce the sulphonating agent before adding the sulphonic acid, together with phosgene and dimethylformamide. Preferably, the calculated amount of sulphonating agent is employed as a mixture with the sulphonic acid.

Pure or industrial sulphonic acids can be employed for the process according to the invention.

Examples of possible impurities caused by the preparation are: water, disulphonic acids, sulphones, sulphone-sulphonic acids, sulphonic acid anhydrides and unreacted starting materials. Furthermore, the sulphonic acids can also contain residues of sulphonating agents or of additives which were used during their preparation in order to prevent sulphone formation.

Sulphonic acids which have been prepared by reacting aromatic compounds with sulphur trioxide in a known manner are preferably used.

Sulphonic acids which have been prepared by reacting aromatic compounds with other sulphonating agents, such as, for example, sulphuric acid, oleum or chlorosulphonic acid, can be employed in the same manner.

If the sulphonic acids employed contain small amounts of sulphonating agent from the preparation, the addition of sulphonating agent is advantageously adjusted thereto.

In general, in the process according to the invention phosgene is used in excess of the stoichiometrically required amount of 1 mol of phosgene per mol of sulphonic acid. An excess of up to 100% of phosgene is usually employed. One can, of course, use larger excesses of phosgene, but in general this brings no advantage. Unreacted, excess phosgene can be recovered and reused.

The process according to the invention is carried out in a manner such that during the reaction phosgene is always present in the reaction mixture in excess, relative to the sulphonic acid.

The process according to the invention is carried out using catalysts from the N,N-dialkylcarboxylic acid amide class. These amides are known compounds, their use is described, for example in U.S. Pat. No. 3,673,247, in French Pat. No. 1,513,906 and in DT-OS (German Published Specification) 1,593,906, 1,963,383 and 2,240,883.

In general, N,N-dialkylcarboxylic acid amides such as, for example, dimethylformamide or dimethylacetamide, preferably dimethylformamide, are preferably used.

The catalysts are generally employed in amounts from 1 to 15%, preferably from 2 to 10%, relative to the weight of the sulphonic acids.

Solvents are not necessary for the process according to the invention. However, one can carry out the reaction using solvents or diluents which are inert towards the reactants. Useful solvents and diluents are mainly halogenohydrocarbons, such as methylene chloride, chloroform or carbon tetrachloride, di-, tri-, tetra- and penta-chloroethane and tri- and tetra-chloroethylene, aromatic compounds, such as, for example, benzene and toluene, especially chlorobenzene and o-, m- and p-dichlorobenzene, and inorganic solvents, such as, for example, liquid sulphur dioxide and excess phosgene. The end product of the process, that is to say the sulphochloride, can also optionally be used as the solvent.

The process according to the invention can be carried out in the temperature range from about 0° C. to 100° C. The range between 20° and 80° C. is preferred and the range between 40° and 70° C. is particularly preferred.

The pressure is not critical for carrying out the process according to the invention. The process can be carried out under normal pressure or elevated or reduced pressure. In general, it is carried out under atmospheric pressure. If low-boiling solvents or a large excess of phosgene is used, the process is carried out under reflux conditions and a pressure corresponding to the required sump temperature.

The process according to the invention can be carried out either discontinuously or continuously.

In carrying out the process discontinuously in a stirred kettle, the catalyst and at least an amount of phosgene equivalent to this are advantageously initially introduced and the sulphonic acid and the phosgene are then metered in such that the latter is always present in the mixture in excess. The sulphonic acid is appropriately added at about the same rate at which the sulphochloride is formed.

The formation of the sulphochloride can be followed by determining the by-products carbon dioxide and hydrogen chloride using known analytical methods.

The process according to the invention can also be carried out continuously in a cascade of stirred kettles. The phosgene, which in this case also must always be present in excess, relative to the sulphonic acids, can be recycled in this procedure.

For the continuous operation one can use a loop reactor into which the phosgene, the sulphonic acid with the sulphonating agent and the catalyst of the N,N-dialkylcarboxylic acid amide series are fed in parallel, while the product is removed at an outlet close to the inlet point.

Another variant of a continuous procedure for the process according to the invention can be carried out using a bubble column. The sulphonic acid, with the sulphonating agent, is then appropriately metered in at the head of the column, and a stream of phosgene is passed countercurrent to this mixture, from the bottom, while the product is removed at the lower region of the column.

The phosgene contained in the off-gas is recovered in a manner which is in itself known, for example by washing with dichlorobenzene. However, it can also be advantageous to carry out the off-gas wash additionally or exclusively with the sulphonic acid, such as benzenesulphonic acid, and/or sulphochloride, such as benzenesulphonyl chloride, and to recycle the phosgene, for example, together with the benzenesulphonic acid.

The crude product is preferably worked up by vacuum distillation. Light volatile components are removed beforehand under a low vacuum or by passing an inert gas in, such as, for example, nitrogen. Excess phosgene and if appropriate the catalyst, which can also be distilled, can be recycled.

A preferred embodiment of the process according to the invention consists in reacting the total amount of the N,N-dialkylcarboxylic acid amide used, for example, as the catalyst with about the same amount by volume of phosgene at room temperature and then to meter in liquid phosgene and the mixture of the sulphonic acid and the sulphonating agent parallel at 50° to 70° C. in a manner such that an excess of phosgene is present.

The hydrogen chloride obtained as a by-product is removed and can optionally be isolated. After the reaction has ended, which can be established by the fact that the evolution of gas ceases, excess phosgene is separated off, catalytically decomposed or recovered in a manner which is in itself known. The reaction mixture which remains is advantageously worked up by fractional distillation under reduced pressure, preferably in the range from 0.1-10 mbars. If the sulphonic acid employed contains high-boiling impurities, such as, for example, diphenyl sulphone, these can be isolated from the distillation residue.

It is surprising that sulphochlorides are formed in virtually quantitative yield in the reaction of benzenesulphonic acid with phosgene in the presence of a sulphonating agent. Compared with the known preparation procedure for aromatic sulphochlorides (DT-OS (German Published Specification) 1,963,383), the process according to the invention has the advantage that the product is obtained in higher purity and in better yield. Furthermore, a smaller amount of catalyst is required in the reaction in the presence of a sulphonating agent.

The by-products carbon dioxide and hydrogen chloride contained in the off-gas of the process can be easily freed from entrained phosgene, for example by catalytic decomposition thereof, by separation over cold traps or, for example, by extraction with solvents, such as, for example, benzene, toluene, chlorobenzene or dichlorobenzene.

The easy working-up of the off-gas causes a slight loading of the environment by the by-products.

EXAMPLE 1 (Comparison Example)

10 g of dimethylformamide are initially introduced into a flask, and about 200 g (140 ml, 2 mols) of phosgene are condensed in a dropping funnel which can be cooled and about 15 ml thereof are slowly added dropwise to the dimethylformamide initially introduced. The temperature in the flask rises to about 40° C. during the exothermic reaction which now proceeds, and a white crystal sludge forms. The flask is warmed to about 50°–70° C. and 158 g (1.0 mol) of molten benzenesulphonic acid (98.9% pure) is added dropwise at this internal temperature in the course of 4 hours. Phosgene is simultaneously metered in at such a rate that it is always in excess in the mixture, relative to the sulphonic acid, which can be recognised by the vigorous reflux. When the dropwise addition is complete, the mixture is stirred at 50°–70° C. for about a further hour, until the evolution of gas has ended, and is left to stand overnight with the cooling discontinued.

Phosgene residues and other volatile constituents in the reaction mixture are stripped off at 60° C. under a water-pump vacuum and the residue is subjected to fractional distillation under an oil-pump vacuum over a mirrored column (3 cm×30 cm). 10.9 g of first runnings, boiling point 95°–97° C./0.7 mm Hg, 141.6 g of main runnings, boiling point 97°–98° C./0.5 mm Hg and 9.2 g of last runnings, boiling point 98°–105° C./0.5–1 mm Hg are obtained. The first runnings and main runnings each contain 99.9% of benzenesulphonyl chloride and the last runnings contain 96.5% of benzenesulphonyl chloride. The total yield is 91.2% of theory, relative to benzenesulphonic acid (100% pure) employed.

EXAMPLES 2 to 8

Examples 2 to 8 were carried out analogously to Example 1 using the same batch size, but a definite amount of sulphuric acid was in each case admixed to the benzenesulphonic acid before use. The essential data can be seen from Table I which follows. The percentage given after the amount of sulphuric acid relates to the amount of the benzenesulphonic acid employed, and the percentage values for the product fractions give the content of benzenesulphonyl chloride (according to gas chromatography).

Table I

| Example | Amount of dimethylformamide | Amount of H$_2$SO$_4$ | | Product fractions | Total yield |
|---|---|---|---|---|---|
| 2 | 10 g | 6.3 g (4%) | I | 127.3 g (99.9% pure) | 95.5% |
|   |      |            | II | 41.5 g (95.5% pure) |       |
| 3 | 10 g | 9.5 g (6%) | I | 168.5 g (99.9% pure) | 97.6% |
|   |      |            | II | 5.1 g (79.6% pure)  |       |
| 4 | 10 g | 11.1 g (7%) | I | 170.8 g (99.9% pure) | 98.5% |
|   |      |            | II | 6.1 g (55.2% pure)  |       |
| 5 | 10 g | 12.6 g (8%) | I | 18.7 g (98.9% pure) | 97.6% |
|   |      |            | II | 148.2 g (99.9% pure) |     |
|   |      |            | III | 9.9 g (58.1% pure) |      |
| 6 | 12 g | 15.8 g (10%) |    | 168.0 g (99.8% pure) | 94.9% |
| 7 | 15 g | 19.0 g (12%) | I | 164.2 g (99.5% pure) | 96.3% |
|   |      |             | II | 13.3 g (50.2% pure) |      |
| 8 | 18 g | 23.7 g (15%) | I | 168.0 g (99.8% pure) | 97.1% |
|   |      |             | II | 15.6 g (24.5% pure) |      |

EXAMPLE 9

Example 9 was carried out analogously to Example 1, with the deviation that 11.1 g (7%) of sulphuric acid were admixed to the dimethylformamide catalyst before adding phosgene and benzenesulphonic acid.

In the distillation, 168.0 g of main runnings, boiling point 100°–102° C./0.5 mm Hg, and 10.1 g of last runnings, boiling point 102°–113° C./5 mm Hg, were obtained.

The main runnings contain 99.8% of benzenesulphonyl chloride and the last runnings contain 54.3% of benzenesulphonyl chloride. The total yield is thus 98.0% of theory, relative to benzenesulphonic acid (100% pure) employed.

EXAMPLES 10 to 13

Examples 10 to 13 were carried out analogously to Example 1 using the same batch size, with the deviation that a definite amount of a sulphonating agent (see Table II) was in each case admixed to the benzenesulphonic acid before use.

Table II

| Example | Sulphonating agent | Product fractions | Total yield |
|---|---|---|---|
| 10 | sulphur trioxide 9.5 g (6%) | I 157.9 g (99.5% pure) II 10.1 g (78.3% pure) | 93.5% |
| 11 | 65% strength oleum 11.1 g (7%) | I 143.9 g (98.8% pure) II 26.2 g (91.2% pure) | 94.0% |
| 12 | chlorosulphonic acid 12.6 g (8%) | I 169.3 g (99.8% pure) II 6.3 g (68.8% pure) | 98.2% |
| 13 | sulphuryl chloride 15.8 g (10%) | 177.8 g (97.5% pure) | 98.2% |

EXAMPLE 14 to 16

Examples 14 to 16 are carried out analogously to Example 4 with the deviation that the dimethylformamide catalyst was initially introduced in a solvent and the reaction is carried out in this solvent (see Table III) at a temperature adjusted to the boiling point thereof.

Table III

| Example | Solvent | Temperature | Product fractions | Total yield |
|---|---|---|---|---|
| 14 | methylene chloride 150 ml | 35°–45° C. | I 170.3 g (99.6% pure) II 6.6 g (73.5% pure) | 98.7% |
| 15 | chloroform 150 ml | 50°–60° C. | I 169.2 g (99.4% pure) II 7.5 g (79.9% pure) | 98.6% |
| 16 | 1,2-dichloroethane 150 ml | 70°–80° C. | I 162.0 g (99.7% pure) II 9.1 g (79.1% pure) | 95.5% |

EXAMPLE 17

624 g (8 mols) of benzene and 8 g of phosphoric acid are initially introduced into a bubble column (vertical reaction tube, 60 cm high, 6 cm wide at the bottom and 10 cm wide in the upper third, gas inlet tube, with a frit, at a height of 4 cm, internal thermometer). The mixture is warmed to 40° C. and subsequently stirred in order to avoid delays in boiling.

A vacuum pump is connected, via two cold traps, to a condenser mounted on the bubble column and the internal pressure of the apparatus is adjusted to 300 mbars.

320 g (4 mols) of liquid sulphur trioxide are added dropwise into a flask, warmed to 80° C., in the course of about 3 hours. The sulphur trioxide thereby vapourises and is passed through the frit into the benzene, where the exothermic reaction immediately proceeds at 40°–50° C. under slight reflux. After the introduction of sulphur trioxide has ended, some of the mixture is separated off for analysis and freed from benzene by distillation.

Analysis: content of 19.7% of organically bonded sulphur, 4.8% of diphenyl sulphone, 1.5% of sulphuric acid and 0.7% of water.

A yield of 93% of theory of benzenesulphonic acid is calculated from this.

In order to carry out the second reaction stage, 5 g of dimethylformamide are initially introduced into a reaction flask and approximately 10 g of condensed phosgene are added dropwise. 25% of the sulphonation mixture obtained above (0.93 mol of benzenesulphonic acid in 1 mol of benzene) and approximately 140 g (1.4 mols) of phosgene are simultaneously added dropwise at an internal temperature of 50°–70° C. in the course of 4 hours. The mixture is stirred at 60° C. for approximately a further hour, until the evolution of gas has ended, and left to stand overnight with the cooling discontinued. The crude product is worked up by distillation analogously to Example 1. 33 g of a 1st fraction, boiling point 30°–40° C./190 mm Hg (98% pure benzene), 0.7 g of a 2nd fraction, boiling point 32°–90° C./2 mm Hg, 135.3 g of a 3rd fraction, boiling point 91°–86° C./1.7–2 mm Hg, and 15.7 g of a 4th fraction, boiling point 96° C./2.5 mm Hg, are obtained.

The 2nd fraction contains 99.2% of benzenesulphonyl chloride, the 3rd fraction contains 99.9% of benzenesulphonyl chloride and the 4th fraction contains 99.7% of benzenesulphonyl chloride.

The phosgenation yield is thus 92.2% of theory and the total yield over the two stages is 86% of theory, relative to sulphur trioxide employed.

EXAMPLE 18

624 g (8 mols) of benzene and 8 g of phosphoric acid are initially introduced into a reaction flask with an internal thermometer, gassing stirrer and reflux condenser. A vacuum pump is connected, via two cold traps, to the condenser and the internal pressure of the apparatus is adjusted to 300 mbars. 320 g (4 mols) of liquid sulphur trioxide are added dropwise into a flask, warmed to 80° C., in the course of three hours. The sulphur trioxide thereby vapourises and is passed, via the gassing stirrer, into the benzene at an internal temperature between 40° and 50° C. After the introduction of sulphur trioxide has ended, the unreacted benzene is distilled off, first under normal pressure and then in vacuo.

Analysis of the sulphonation product: 18.7% of organic S (20.3% in theory), 8.9% of diphenyl sulphone, 3.9% of sulphuric acid and 0.3% of water.

A sulphonation yield of 87% of theory of benzenesulphonic acid thus results.

The reaction of the sulphonation product with phosgene is carried out analogously to Example 17, but at an internal temperature between 20° and 30° C. 12 g of sulphuric acid are added to the sulphonation product before the phosgenation. 22 g of dimethylformamide catalyst are employed.

After working up by distillation, 215.5 g of a 1st fraction, boiling point 109°–111° C./1.5 mm Hg, and 15.0 g of a 2nd fraction, boiling point 111°–115° C./4 mm Hg, are obtained.

The fraction contains 99.1% of benzenesulphonyl chloride and the second fraction contains 75.0% of benzenesulphonyl chloride.

The phosgenation yield is thus 97.5%, for a batch size of 1.30 mols in the second stage; the total yield over two stages is 85% of theory, relative to sulphur trioxide employed.

What is claimed is:

1. In a process for the preparation of sulphonic acid chloride of the formula

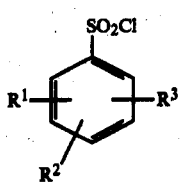

wherein $R^1$, $R^2$ and $R^3$ are identical or different and denote hydrogen, a lower alkyl radical or a cycloalkyl radical, halogen, nitro, aryl, aralkyl, aryl ether or a radical

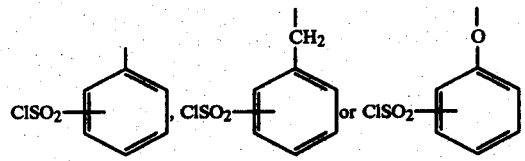

or wherein adjacent radicals $R^1$ and $R^2$ are linked to form a cycloaliphatic or aromatic carbocyclic ring which is optionally substituted by a sulphonic acid chloride group, by contacting a sulphonic acid of the formula

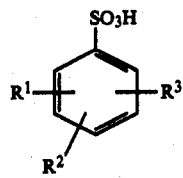

wherein $R^1$, $R^2$ and $R^3$ have the above-described meanings with phosgene in the presence of N,N-dialkylcarboxylic acid amide catalyst, the improvement which comprises carrying out the process in the presence of a sulphonating agent.

2. A process according to claim 1 wherein the sulphonating agent is sulphuric acid, sulphur trioxide, chlorosulphonic acid, sulphuryl chloride or a mixture thereof.

3. A process according to claim 1 wherein the sulphonating agent is present in the amount up to 15 percent by weight based upon the amount of sulphonic acid employed.

4. A process according to claim 1 wherein the reaction is carried out at a temperature up to 100° C.

5. A process according to claim 1 wherein $R^1$, $R^2$ and $R^3$ are identical or different and represent a lower alkyl radical of 1 to 6 carbon atoms, a cycloalkyl radical having 5 to 6 carboxylic carbon atoms, halogen, a phenyl or naphthyl aryl radical, an aralkyl radical having 6 to 18 carbon atoms, the aliphatic part of which contains 1 to 6 carbon atoms and the aromatic part of which is benzene or $R^1$ and $R^2$ together form a fused ring which fused ring is an indane, tetralin, indene or naphthalene ring and wherein $R^1$ to $R^3$ can be optionally substituted with a further radical selected from the group consisting of halogen, nitro, lower alkyl, aryl, alkoxy and aralkyl.

* * * * *

UNITED STATES PATENT AND TRADEMARK OFFICE
CERTIFICATE OF CORRECTION

PATENT NO. : 4215071
DATED : July 29, 1980
INVENTOR(S) : HEINZ U. BLANK and THEODOR PFISTER It is certified that error appears in the above—identified patent and that said Letters Patent is hereby corrected as shown below:

| COLUMN | LINE | |
|---|---|---|
| 1 | 7 | "shown" should read --known--. |

Signed and Sealed this

Eleventh Day of November 1980

[SEAL]

Attest:

SIDNEY A. DIAMOND

Attesting Officer

Commissioner of Patents and Trademark